United States Patent [19]

Martin

[11] 4,070,389
[45] Jan. 24, 1978

[54] PHENYLGLYOXYLONITRILE-2-OXIME-CYANOMETHYLETHER

[75] Inventor: Henry Martin, Allschwil, Switzerland

[73] Assignee: Ciba-Geigy Corporation, Ardsley, N.Y.

[21] Appl. No.: 717,792

[22] Filed: Aug. 25, 1976

[30] Foreign Application Priority Data

Sept. 4, 1975 Switzerland .............. 11458/75

[51] Int. Cl.$^2$ .......................................... C07C 121/84
[52] U.S. Cl. ................... 260/465 E; 71/77; 71/93; 71/98; 71/100; 71/103; 71/105; 71/106; 71/111; 71/115; 71/116; 71/118; 71/120
[58] Field of Search .............. 260/465 E; 71/105, 121, 71/77

[56] References Cited

U.S. PATENT DOCUMENTS

| | | | |
|---|---|---|---|
| 3,234,255 | 2/1966 | Hackman et al. ................. | 71/121 |
| 3,483,246 | 12/1969 | Kaufman ............................ | 71/105 |
| 3,515,536 | 6/1970 | Hill et al. .......................... | 71/121 |
| 3,799,757 | 3/1974 | Dixon et al. ...................... | 71/105 |
| 3,869,278 | 3/1975 | Wilcox ............................... | 71/121 |
| 3,914,300 | 10/1975 | Haddock et al. ................. | 71/121 |

*Primary Examiner*—Glennon H. Hollrah
*Attorney, Agent, or Firm*—Harry Falber

[57] ABSTRACT

This invention concerns the new compound phenylglyoxylonitrile-2-oxime-cyanomethylether of formula

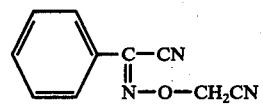

and compositions containing it, to be used as safener (antidote) for selectively combatting weeds in culture crops, especially millet and rice, in order to protect these cultivated plants from being injured by strong herbicides such as chloroacetanilides and thiolcarbamates.

1 Claim, No Drawings

PHENYLGLYOXYLONITRILE-2-OXIME-CYANOMETHYLETHER

The present invention relates to a novel oxime ether, to processes for producing it, to its use as an antidote (safener) for herbicides which damage certain cultivated plants, so that such herbicides can be employed as selective herbicides, without loss of their herbicidal action against weeds, in crops of these cultivated plants; the invention relates also to compositions containing the said oxime ether, optionally together with a herbicide.

It is known that herbicides of the most varied classes of substances, such as triazines, urea derivatives, carbamates, thiolcarbamates, halogenoacetanilides, halogenophenoxyacetic acids, etc., have in the case of cultivated plants an action that is not selective or insufficiently selective, with the result that these herbicides attack not only the weeds to be combatted but to a lesser or greater extent also the cultivated plants.

Various substances have already been suggested for overcoming this problem, which substances are able to specifically antagonise the harmful action of the herbicide on the cultivated plant, i.e. to protect the cultivated plant without noticeably affecting the herbicidal action on the weeds to be combatted. Depending on its properties, the antidote can be used before emergence (pre-emergence) or after emergence (post-emergence) of the plants: it can be used for pretreatment of the seed of the cultivated plant (seed dressing); or it can be applied into the seed furrows before sowing; or it can be used for the pretreatment of cuttings; or finally it can be applied as a tank mixture; whereby it can be employed on its own or together with the herbicide, and can be applied either by one or by several of these methods. The treatment with the antidote can be carried out before or after the herbicidal treatment, or the two treatments can be performed simultaneously. the pre-emergence treatment includes both the treatment of the cultivated area before sowing (ppi = pre plant incorporation) and the treatment of the sown cultivated area before emergence of the plants.

The suggested antidotes frequently have an action that is very "specific to the species" with regard to the cultivated plants (e.g. maize, cereals such as wheat, etc., rice, sorghum, soybean, cotton, sugar cane, etc.) and with regard to the type of active substance of the herbicide (triazines, carbamates, etc.) and often also with regard to the type of application (seed dressing, pre-emergence tank application, etc.), i.e. a specific antidote is frequently suitable only for a specific cultivated plant and for certain herbicidal classes of active substance.

Thus the British Pat. No. 1,277,557 describes the protective treatment of seed and of shoots of wheat and sorghum with certain oxamic acid esters and amides in order to avoid the harm caused by "Alachlor" (N-methoxymethyl-(2',6'-diethyl-chloroacetanilide). According to other references (DOS 1,952,910, DOS 2,245,471, French Pat. No. 2,021,611), antidotes are suggested for the treatment of cereals, maize seed and rice seed for protection against the attack from herbicidal thiolcarbamates. In DP No. 1,576,676 and U.S. Pat. No. 3,131,509, there are suggested hydroxy-aminoacetanilides and hydantoins for the protection of the seed of cereals against carbamates such as IPC, CIPC, etc.

The direct treatment of certain useful plants before or after emergence of the plants on a cultivated area with antidotes as antagonists of specific classes of herbicides is described in DOS Nos. 2,141,586 and 2,218,097 and in U.S. Pat. No. 3,867,444.

Whilst maize plants can be excellently protected from damage that can result from strongly herbicidally effective chloroacetanilides, such as have been described in DOS Nos. 2,212,268, 2,305,495 and 2,328,340, by an N-substituted dichloroacetamide being applied as antidote to the soil (DOS No. 2,402,983), corresponding tests in other crops, such as cultivated millet and rice, have been unsuccessful.

It has now been found that surprisingly the novel oxime ether of formula I

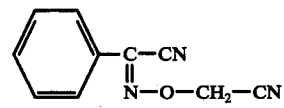

(I), which can be designated as [O-(cyanomethyl)-oximino]-benzylcyanide or as [O-(cyanomethyl)-oximino]-α-cyanotoluene or as phenylglyoxylonitrile-2-oxime-cyanomethyl ether, is excellently suitable for the protection of cultivated plants, such as maize, varieties of cereals (wheat, rye, barley, oats, etc.), cotton, sugar beet, sugar cane, soybean, etc., especially however cultivated millet of the sorghum genus, such as S. vulgare and S. hybridium, as well as rice, from the attack of herbicides of the most varied classes of substances, such as triazines, phenylureas, carbamates, benzoic acid derivatives, halogenophenoxyacetic acids, etc., particularly however from the attack of herbicidal halogenoacetanilides and thiolcarbamates.

The free phenylglyoxylonitrile-2-oxime from which the above ether derives and some ring-substituted derivatives of the free oxime are described in U.S. Pat. No. 3,799,757 as growth inhibitors for regulating the growth in height of maize, cereals and soybean, i.e. for a completely different field of application.

The novel oxime ether of formula I is produced according to the invention by reaction of a salt, especially of an alkali metal salt, of phenylglyoxynitrile-2-oxime of formula II

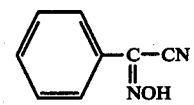

(II)

with a cyanomethyl halide (halogenoacetonitrile) of the formula Hal—CH$_2$—CN.

The starting oxime of formula II is known and can be produced, for example, according to "Organic Reactions" (1953), Vol. 7, pp. 343 and 373. It is known that oximes can exist in two stereoisomeric forms, the syn- and anti-form. Also the oxime ether of formula I according to the invention can exist in both forms and as a mixture thereof. Accordingly, within the scope of the present description are meant both stereoisomeric forms either separately or as a mixture in any reciprocal mixture ratio.

The following Example illustrates the production of the novel oxime ether of formula I.

EXAMPLE 33.8 g of phenylglyoxylonitrile-2-oxime (sodium salt) is suspended in 200 ml of acetonitrile in a 350 ml sulphonating flask. An addition is then made dropwise of 15.1 g of chloroacetonitrile in 20 ml of acetonitrile, whereupon a very slight increase in temperature can be observed. The suspension is subsequently refluxed with stirring for 3 hours, during the process of which the reaction mixture assumes a light-green colour. After cooling to room temperature, the formed sodium chloride is filtered off with suction, and the filtrate is concentrated in a rotary evaporator to obtain as residue 31 g of crude product. This is dissolved in 200 ml of acetonitrile; the solution is stirred with charcoal and filtered until clear. Concentration of the filtrate in the rotary evaporator yields 25.4 g of oxime ether (68.6% of theory), m.p. 53° – 54° C.

Recrystallised from isopropanol, the pure phenyl-glyoxylonitrile-2-oxime-cyanomethyl ether melts at 56° – 57° C (syn-form). The other stereoisomeric form (anti) of this ether melts at 58°–59° C and has a boiling point of 136° C/0.05 torr.

Chloroacetanilides usable as highly effective active substances which on their own damage cultivated plants, such as cereals, maize, rice and cultivated millet varieties, but which when used together with the oxime ether according to the invention no longer appreciably attack these cultivated plants whilst retaining the herbicial effectiveness against weeds, have become known, for example, from DOS Nos. 2,212,268, 2,305,495, 2,328,340, 2,402,983, 2,405,183 and 2,405,479.

The antidote according to the invention is preferably used together with herbicidal chloroacetanilides which correspond to the formula

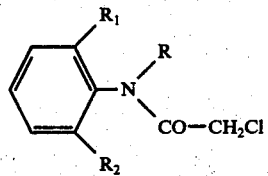

wherein $R_1$ and $R_2$ independently of one another are hydrogen, a lower alkyl, halogenoalkyl, alkoxy, alkoxyalkyl or alkylthioalkyl group or a halogen atom, and R is an alkyl group having 1 to 4 C atoms which is substituted by carboxy, carboxylic acid ester, carboxylic acid amide or cyano groups, or an alkoxyalkyl group of the form —A—O—$R_3$, wherein A is an alkylene group having 1 to 4 C atoms of which 1 or 2 are in the direct chain, and $R_3$ is a lower alkyl or alkenyl group or a cycloalkyl or cycloalkylmethyl group having 3 to 6 ring carbon atoms, whereby furthermore the phenyl nucleus can also carry one or two substituents in the meta position with respect to the aniline nitrogen atom which are of the definition given for $R_1$ and $R_2$.

Herbicidal chloroacetanilides preferably used are those where in the above formula $R_1$ is hydrogen or an alkyl group having 1 to 4 C atoms, $R_2$ is an alkyl group having 1 to 4 C atoms, R is an alkyl group having 1 to 4 C atoms which is substituted by carboxylic acid ester groups, or an alkoxyalkyl group of the formula —A—O—$R_3$, wherein A is an alkylene group having 2 or 3 C atoms of which 1 or 2 are in the direct chain, and $R_3$ is an alkyl or alkenyl group having 1 to 4 C atoms, whereby furthermore the phenyl nucleus can also carry a lower alkyl or alkoxy group in the meta position to the aniline nitrogen atom.

Some herbicidal chloroacetanilides which can be used are listed below:
N-(2'-methoxyethyl)-2,6-dimethyl-chloroacetanilide,
N-(2-allyloxyethyl)-2,6-dimethyl-chloroacetanilide,
N-(2'-n-propyloxyethyl)-2,6-dimethyl-chloroacetanilide,
N-(2'-isopropyloxyethyl)-2,6-dimethyl-chloroacetanilide,
N-(2'-methoxyethyl)-2-methyl-6-ethyl-chloroacetanilide,
N-(2'-methoxyethyl)-2,6-diethyl-chloroacetanilide,
N-(2'-ethoxyethyl)-2-methyl-6-ethyl-chloroacetanilide,
N-(1'-ethoxycarbonyl-ethyl)-2,6-dimethyl-chloroacetanilide,
N-(3'-methoxy-propyl-(2')-2-methyl-chloroacetanilide,
N-(3'-methoxy-propyl-(2')-2,6-dimethyl-chloroacetanilide,
N-(3'-methoxy-propyl-(2')-2-methyl-6-ethyl-chloroacetanilide,
N-(3'-methoxy-propyl-(2')-2,6-diethyl-chloroacetanilide,
N-(3'-methoxy-propyl-(2')-2-ethyl-chloroacetanilide,
N-(2'-ethoxyethyl)-2,6-diethyl-chloroacetanilide,
N-(2'-n-propoxyethyl)-2-methyl-6-ethyl-chloroacetanilide,
N-(2'-n-propoxyethyl)-2,6-diethyl-chloroacetanilide,
N-(2'-isopropyloxyethyl)-2-methyl-6-ethyl-chloroacetanilide,
N-chloroacetyl-2,6-dimethylanilino-acetic acid ethyl and
N-chloroacetyl-2,6-dimethylanilino-acetic acid methyl ester,
β-(N-chloroacetyl-2,6-dimethylanilino)-propionic acid methyl ester,
α-(N-chloroacetyl-2-methyl-6-ethyl-anilino)-propionic acid ethyl ester,
N-(3'-methoxy-propyl-(2')-2,3-dimethyl-chloroacetanilide,
N-(2'-ethoxyethyl)-2-methyl-6-chloroacetanilide,
N-(2'-methoxyethyl)-2-methyl-6-chloroacetanilide,
N-(2'-methoxyethyl)-2-methyl-6-methoxy-chloroacetanilide.

The herbicidal chloroacetanilides mentioned above and other herbicidal chloroacetanilides of this type and the production thereof have been described in the aforementioned German 'Offenlegungsschriften'.

Suitable thiolcarbamates which can be used as herbicides, especially in the case of pretreatment of the seed with the novel oxime ether, are those of the general type:

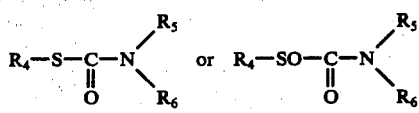

wherein $R_4$ is a lower alkyl group, and $R_5$ and $R_6$ are two identical lower alkyl groups having at least 3 carbon atoms;

the following may for example be mentioned:
S-ethyl-N,N-dipropylthiocarbamate and
S-ethyl-N,N-diisobutylthiocarbamate.

Further examples of utilisable herbicidal thiolcarbamates are disclosed by the U.S. Pat. Nos. 2,913,327, 3,037,853, 3,175,897, 3,185,720, 3,198,786 and 3,582,314.

The applied amount of the antidote varies between about 0.01 and about 15 parts by weight per part by weight of halogenoacetanilide or thiolcarbamate. The most suitable ratio with regard to the optimum action in the case of the specific cultivated plant is determined from case to case, i.e. depending on the employed chloroacetanilide or thiolcarbamate.

As mentioned initially, various methods and techniques can be employed for the use of the novel antidote of formula I together with herbicidal active substances or mixtures of active substances of the chloroacetanilide class and/or of the thiolcarbamate class.

1. Seed dressing
  a. Dressing of the seed with an antidote formulated as a wettable powder by shaking of the constituents in a vessel until there exists a uniform distribution over the surface of the seeds (dry dressing). The amount of antidote used for this purpose is about 10 to 500 g (40 g to 2 kg of wettable powder) per 100 kg of seed.
  b. Dressing of the seed with an emulsion concentrate of the antidote by the method and with the amounts given under (a) (wet dressing).
  c. Dressing by immersion of the seed in a liquor containing 50–3200 ppm of antidote for 1–20 hours and subsequent drying of the seed (immersion dressing).

2. Application as tank mixture
A liquid preparation of a mixture of antidote and herbicide (quantitative ratio between 10:1 and 1:10) is used, with the applied amount of herbicide being 0.1 to 10 kg per hectare. This tank mixture is preferably applied before emergence (either before or after sowing), or it is worked into the unsown soil to a depth of 5–10 cm.

3. Application into the seed furrow
The antidote is introduced, as an emulsion concentrate, wettable powder or granulate, into the open sown seed furrow and, after the covering of the seed furrow in the normal manner, the herbicide is applied either before or after emergence of the plants.

The antidote can therefore be applied before, together with, or after the herbicide, and its application to the seeds or to the field before emergence can be effected either before or after sowing; or in certain cases it can be effected also after germination of the seed (post-emergence).

If the antidote is applied simultaneously with the herbicide, this is accomplished by the use of a preparation according to the invention, which preparation contains the oxime ether of formula I and at least one herbicide from the chloroacetanilide and/or thiolcarbamate class, together with additives such as carriers and/or distribution agents.

The process according to the invention for the selective control of weeds in cultivated crops, especially of the sorghum and rice genera, is such that the seeds of the cultivated plants or the cultivated areas intended for sowing or already sown, or on which the sown plants have already emerged, are treated, simultaneously, or successively in any desired sequence and at a suitable interval of time, on the one hand with phenylglyoxylonitrile-2-oxime-cyanomethyl ether of formula I as the antidote protecting the cultivated plants or the seed thereof, and on the other hand with at least one herbicidal active substance, preferably of the chloroacetanilide class and/or of the thiolcarbamate class.

The compositions used, which contain herbicide and antidote separately or together, can be in any suitable conventional form. They can be produced in a manner known per se by the intimate mixing and grinding of the active substance(s) (including antidote) with suitable carriers and/or distributing agents, optionally with the addition of dispersing agents or solvents.

The usual forms of such compositions are either solid, such as dusts, scattering agents and granulates, or liquid, such as solutions and aqueous dispersions; or they are water-dispersible concentrates of active substance, such as wettable powders, emulsion concentrates or pastes.

In addition to the "safener" action of the antidote of formula I according to the invention, there is observed a certain antagonising counteraction moreover on the growth-inhibiting effect of some growth regulators on grasses in the case of overdosage of the growth inhibitor. Furthermore, the compound of formula I, used on its own, exhibits a germination-stimulating action on certain seed varieties, such as those of sorghum, rice, etc.

The following tests were carried out to determine the selective herbicidal action of a highly effective first-class herbicidal product of the chloroacetanilide class, on its own or together with the antidote of formula I according to the invention; N-[3'-methoxypropyl-(2')-2-methyl-6-ethyl-chloroacetanilide (DOS 2,328,340) of the formula

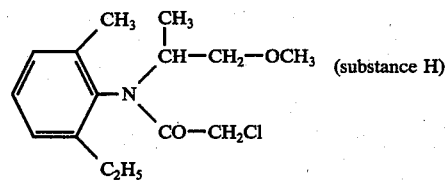 (substance H)

was used as the herbicidal active substance.

1. Pre-emergence application as tank mixture
  a. After sowing
Aqueous stock liquors (suspensions) from formulated wettable powders of the herbicide (substance H) and the antidote of formula I (substance S) according to the invention were produced; and these were then applied, both on their own and as mixtures at the given concentrations and in the given mixture ratios, directly after the sowing of various varieties of cultivated millet, namely Sorghum hybridum (varieties "Funk", "Dekalb", "NK 222" and "DC 59"), in pots or in seed trays in the greenhouse, the said liquors being applied to the surface of the soil in the sown vessels. The pots or seed trays were then kept at 22° – 23° C with the required amount of watering, and the results were evaluated after 15 days according to the following ratings:

9 = plants undamaged (as in the case of the untreated control plants),
1 = plants completely destroyed,
2 – 8 = intermediate stages of damage.
  b. Before sowing (PPI)
In the same manner as under (a), soil in pots and in seed trays was treated with the liquors containing the active substance, and immediately afterwards these vessels were sown with seed of the millet variety "Funk".

The results are summarised in the following Table I. The concentration values in kg/hectare in relation to the other units of measure are as follows:

1 kg/hectare = 0.1 g/m² = 2 mg per liter of soil (since seed trays and pots are filled with soil to a depth of 5 cm).

Table I

| Applied concentration in kg/hectare | | after sowing | | | before sowing | | | | | | | | | | | |
|---|---|---|---|---|---|---|---|---|---|---|---|---|---|---|---|---|
| Substance | | Funk b | | | Funk a | | | Dekalb | | | NK222 | | | DC59 | | |
| H | S | H | H+S | S | H | H+S | S | H | H+S | S | H | H+S | S | H | H+S | S |
| 2,0 | 4,0 | 1 | 9 | 9 | | | | | | | | | | | | |
| 2,0 | 2,0 | 1 | 9 | 9 | | | | | | | | | | | | |
| 4,0 | 16,0 | | | | 1 | 8 | 9 | 1 | 8 | 9 | 1 | 9 | 9 | 2 | 9 | 9 |
| 4,0 | 8,0 | | | | | 6 | | | 6 | | | 6 | | | 6 | |
| 2,0 | 8,0 | | | | 2 | 9 | 9 | 2 | 9 | 9 | 2 | 9 | 9 | 2 | 9 | 9 |
| 2,0 | 4,0 | | | | | 8 | 9 | | 8 | 9 | | 9 | 9 | | 9 | 9 |

It is seen that the cultivated millet varieties remain virtually unaffected with the application of various mixture ratios H : S at the different concentrations, whereas with application of the herbicide H alone they are completely destroyed even at low concentrations.

2. Seed dressing (wet)

Aqueous emulsion concentrates (liquid) of the antidote according to the invention were prepared, and the cultivated-millet seed (50 g of seed) in a bottle was treated therewith by shaking. The various concentrations of antidote were expressed in grams of antidote per 100 kg of seed. Shortly after this dressing treatment, the seed was sown in pots or in seed trays and then treated in the usual manner (pre-emergence) as described under a). The results were evaluated 15 days after application of the herbicide using the same ratings as before; the results are listed in the following Table II.

Table II

| Applied concentration | | | | | | | | | | | | | | |
|---|---|---|---|---|---|---|---|---|---|---|---|---|---|---|
| Substance S g/100 kg of seed | Herbicide H kg/hectare | Variety of Sorghum hybridum | | | | | | | | | | | | |
| | | Funk | | | Dekalb | | | NK222 | | | DC59 | | | |
| | | H | H+S | S | H | H+S | S | H | H+S | S | H | H+S | S | |
| 150 | 4 | 1 | 8 | 8 | 1 | 5 | 9 | 1 | 5 | 8 | 2 | 5 | 8 | |
| 75 | 4 | | 9 | 9 | | 7 | 9 | | 8 | 9 | | 8 | 9 | |
| 37,5 | 4 | | 9 | 9 | | 3 | 9 | | 6 | 9 | | 7 | 9 | |
| 150 | 2 | 2 | 9 | | 2 | 8 | | 2 | 8 | | 2 | 8 | | |
| 75 | 2 | | 9 | | | 9 | | | 9 | | | 9 | | |
| 37,5 | 2 | | 9 | | | 9 | | | 9 | | | 9 | | |

It is seen here too that complete protection of the cultivated millet is obtained where the concentration of herbicide H is low, but sufficiently high to combat weeds, even with low applied amounts of the antidote S. With higher doses of herbicide the results are somewhat different depending on the variety of cultivated millet used; however, in the case of the "Funk" variety the results are still optimum.

It was possible also in field tests to confirm these excellent results, whereby it was shown that still better results can be obtained with the seed dressing method than with the tank mixture method.

The antagonistic action of the antidote according to the invention does not however extend to the main weeds normally associated with cultivated plants, e.g. Echinochloa, Setaria italica, Digitaria sanguinalis, etc. These weeds are destroyed by the herbicides used with the antidote practically to the same high degree as that resulting without the presence of the antidote.

Also insecticides, fungicides, etc., such as "Diazinon", "Captan", "Methoxychlor" and so forth, do not lose their effectiveness as a result of the antidote; such insecticides can therefore be concomitantly used in seed dressing.

Good "safening" effects similar to those resulting with the use of the herbicide H can be obtained when the oxime ether according to the invention is employed with thiolcarbamates and with other chloroacetanilides even on other crops, as is shown by the following test with rice where N-[2-n-propyloxyethyl]-2,6-diethyl-chloroacetanilide of the formula

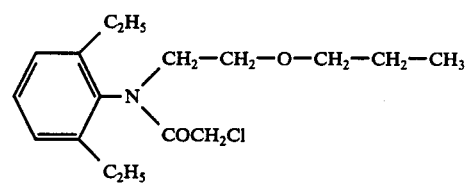

is used as the herbicide (K).

Rice is grown in very moist soil until the plants are carrying 3 to 4 leaves. The plants are then taken from the soil and the adhering soil is washed from the roots with water. The roots are thereupon immersed for 30 minutes in aqueous preparations containing respectively 125, 32, 8 and 2 ppm (= parts of active substance per $10^6$ parts of the "solution") of the antidote, phenylglyoxylonitrile-2-oxime-cyanomethyl ether.

The rice plants treated in this manner are then planted in soil in containers having a surface area of 12 cm × 8 cm and a depth of 15 cm (96 cm² surface area and 1.44 liters volume per container). The height of water is subsequently adjusted to 2 cm. Spraying is carried out after 10 days with a 0.4% liquor of the herbicide K [N-(2'-n-propyloxyethyl)-2,6-diethyl-N-chloroacetanilide], the equivalent amount of liquor being 500 liters per hectare of 2 kg/hectare (= 0.5 cm³ of liquor per container). The liquor is sprayed over the leaves of the rice plants and into the water. The test is evaluated 20 days after the treatment with the herbicide. Evaluation is on the basis of the scale of ratings used in the test with millet (9 = normal condition; 1 = completely destroyed).

The results are summarized in the following table:

| Conc. herbicide K | Conc. antidote S | Toxicities on rice K (alone) | K + S | S (alone) |
|---|---|---|---|---|
| 2 kg/ha | 2 ppm | 4 | 8 | 9 |
What is claimed is:
1. The compound phenylglyoxylonitrile-2-oxime-cyanomethyl ether of the formula.
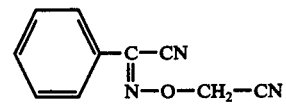

| | | Toxicities on rice | | |
|---|---|---|---|---|
| Conc. herbicide K | Conc. antidote S | K (alone) | K + S | S (alone) |
| 2 kg/ha | 125 ppm | 4 | 8 | 9 |
| 2 kg/ha | 32 ppm | 4 | 7 | 9 |
| 2 kg/ha | 8 ppm | 4 | 8 | 9 |